(12) United States Patent
Park

(10) Patent No.: US 11,111,480 B2
(45) Date of Patent: *Sep. 7, 2021

(54) CULTURE MEDIA FOR MULTIPOTENT STEM CELLS

(71) Applicant: HOPE BIOSCIENCES, LLC, Sugar Land, TX (US)

(72) Inventor: Hyeonggeun Park, Sugar Land, TX (US)

(73) Assignee: HOPE BIOSCTENCES, LLC, Sugar Land, TX (US)

(*) Notice: Subject to any disclaimer, the term of this patent is extended or adjusted under 35 U.S.C. 154(b) by 0 days.

This patent is subject to a terminal disclaimer.

(21) Appl. No.: 16/173,962

(22) Filed: Oct. 29, 2018

(65) Prior Publication Data

US 2019/0071642 A1    Mar. 7, 2019

Related U.S. Application Data

(63) Continuation of application No. PCT/US2017/030410, filed on May 1, 2017, which is a continuation-in-part of application No. 15/460,111, filed on Mar. 15, 2017, and a continuation-in-part of application No. 15/142,135, filed on Apr. 29, 2016, now Pat. No. 10,513,689.

(51) Int. Cl.
*C12N 5/0775* (2010.01)

(52) U.S. Cl.
CPC ......... *C12N 5/0663* (2013.01); *C12N 5/0665* (2013.01); *C12N 5/0667* (2013.01); *C12N 5/0668* (2013.01); *C12N 2500/25* (2013.01); *C12N 2500/32* (2013.01); *C12N 2500/99* (2013.01); *C12N 2501/11* (2013.01); *C12N 2501/113* (2013.01); *C12N 2501/115* (2013.01); *C12N 2501/125* (2013.01); *C12N 2501/31* (2013.01); *C12N 2501/33* (2013.01); *C12N 2501/39* (2013.01)

(58) Field of Classification Search
CPC .. C12N 5/0665; C12N 5/0667; C12N 5/0668; C12N 2500/25; C12N 2500/32; C12N 2500/99; C12N 2501/11; C12N 2501/113; C12N 2501/115; C12N 2501/125; C12N 2501/31; C12N 2501/33; C12N 2501/39; C12N 5/0663

USPC ......................................................... 435/384
See application file for complete search history.

(56) References Cited

U.S. PATENT DOCUMENTS

| | | | |
|---|---|---|---|
| 7,807,461 B2 | 10/2010 | Kang et al. | |
| 8,252,591 B2 | 8/2012 | Ince et al. | |
| 8,871,513 B2* | 10/2014 | Ra | C12N 5/0605 |
| | | | 435/405 |
| 2004/0037811 A1 | 2/2004 | Penn et al. | |
| 2007/0026520 A1* | 2/2007 | Kelly | C12N 5/0611 |
| | | | 435/366 |
| 2007/0128685 A1 | 6/2007 | Faudoa et al. | |
| 2008/0085555 A1 | 4/2008 | Asahara et al. | |
| 2010/0003265 A1 | 1/2010 | Scheffler et al. | |
| 2013/0089928 A1 | 4/2013 | An et al. | |
| 2013/0217129 A1 | 8/2013 | Naughton et al. | |
| 2014/0170748 A1 | 6/2014 | Bhatia et al. | |
| 2015/0064273 A1 | 3/2015 | Peled et al. | |

FOREIGN PATENT DOCUMENTS

| | | |
|---|---|---|
| WO | 2007123363 A1 | 11/2007 |
| WO | 2013032052 A1 | 3/2013 |

OTHER PUBLICATIONS

Wager, et al. Replicative Senescence of Mesenchymal Stem Cells: A Continuous and Organized Process, PLoS ONE. 3(5):e2213 (2008).

Broxmeyer et al., Stromal cell-derived factor-1/CXCL12 directly enhances survival/antiapoptosis of myeloid progenitor cells through CXCR4 and proteins and enhances engraftment of competitive, repopulating stem cells, Journal of Leukocyte Biology, vol. 73, May 2003, pp. 630-638.

* cited by examiner

*Primary Examiner* — Jennifer M. H. Tichy

(74) *Attorney, Agent, or Firm* — Rao DeBoer Osterrieder, PLLC; Dileep P. Rao

(57) ABSTRACT

A growth medium for culturing mesenchymal stem cells. The medium comprises a serum, a fibroblast growth factor, and either an L-cysteine, a glutathione, or an N-acetyl cysteine. Optionally, the medium can comprise various quantities of an epidermal growth factor, a hydrocortisone, a calcium chloride, an insulin, a pituitary extract, a selenium, a stromal-derived factor, a sodium pyruvate, a transferrin, and serum-free medium.

8 Claims, 3 Drawing Sheets

FIG. 1

| REAGENTS | COMPONENT RANGES | A SAMPLE EMBODIMENT |
|---|---|---|
| SERUM FREE MEDIUM | BALANCE TO 100% VOL | BALANCE TO 100% VOL |
| SERUM | 0.1 ~ 50% VOL | ~ 10% VOL |
| FIBROBLAST GROWTH FACTOR | 1 pg/mL ~ 100 ng/mL | 1 ~ 10 ng/mL |
| EPIDERMAL GROWTH FACTOR | 1 pg/mL ~ 100 ng/mL | 1 ~ 10 ng/mL |
| HYDROCORTISONE | 1 pg/mL ~ 100 µg/mL | 10 ~ 100 ng/mL |
| CALCIUM CHLORIDE | 1 nM ~ 100 mM | 0.01 ~ 0.1 mM |
| INSULIN | 1 ng/mL ~ 100 mg/mL | 0.5 ~ 5 mg/mL |
| PITUITARY EXTRACT | 1 pg/mL ~ 100 mg/mL | 10 ~ 100 µg/mL |
| L-CYSTEINE OR GLUTATHIONE | 1 nM ~ 100 mM | 0.5 ~ 5 mM |
| SELENIUM | 1 pg/mL ~ 100 mg/mL | 0.1 ~ 1 µg/mL |
| STROMAL CELL-DERIVED FACTOR | 1 pg/mL ~ 100 ng/mL | 1 ~ 10 ng/mL |
| SODIUM PYRUVATE | 1 ng/mL ~ 100 mg/mL | 2 ~ 20 mg/mL |
| TRANSFERRIN | 1 ng/mL ~ 100 mg/mL | 0.1 ~ 1 mg/mL |

FIG. 2

| REAGENTS | COMPONENT RANGES | A SAMPLE EMBODIMENT |
|---|---|---|
| EPIDERMAL GROWTH FACTOR | 1 pg/mL ~ 100 ng/mL | FROM ABOUT 1 pg/mL TO ABOUT 100 ng/mL |
| HYDROCORTISONE | 1 pg/mL ~ 100 µg/mL | FROM ABOUT 1 pg/mL TO ABOUT 100 µg/mL |
| CALCIUM CHLORIDE | 1 nM ~ 100 mM | FROM ABOUT 1 nM TO ABOUT 100 mM |
| INSULIN | 1 ng/mL ~ 100 mg/mL | FROM ABOUT 1 ng/mL TO ABOUT 100 mg/mL |
| PITUITARY EXTRACT | 1 pg/mL ~ 100 mg/mL | FROM ABOUT 1 pg/mL TO ABOUT 100 mg/mL |
| SELENIUM | 1 pg/mL ~ 100 mg/mL | FROM ABOUT 1 pg/mL TO ABOUT 100 mg/mL |
| STROMAL CELL-DERIVED FACTOR | 1 pg/mL ~ 100 ng/mL | FROM ABOUT 1 pg/mL TO ABOUT 100 ng/mL |
| SODIUM PYRUVATE | 1 ng/mL ~ 100 mg/mL | FROM ABOUT 1 ng/mL TO ABOUT 100 mg/mL |
| TRANSFERRIN | 1 ng/mL ~ 100 mg/mL | FROM ABOUT 1 ng/mL TO ABOUT 100 mg/mL |
| SERUM FREE MEDIUM | BALANCE TO 100% VOL | BALANCE TO 100% VOL |

FIG. 3

| REAGENTS | COMPONENT RANGES | A SAMPLE EMBODIMENT |
|---|---|---|
| MINIMUM ESSENTIAL MEDIUM | BALANCE TO 100% VOL | BALANCE TO 100% VOL |
| SERUM | FROM ABOUT 0.1 TO ABOUT 50% VOL | ~ 10% VOL |
| L-CYSTEINE OR GLUTATHIONE | FROM ABOUT 1 nM TO ABOUT 100 mM | 0.5 ~ 5 mM |
| INSULIN | FROM ABOUT 1 ng/mL TO ABOUT 100 mg/mL | 0.5 ~ 5 mg/mL |
| SELENIUM | FROM ABOUT 1 pg/mL TO ABOUT 100 mg/mL | 0.1 ~ 1 µg/mL |
| SODIUM PYRUVATE | FROM ABOUT 1 ng/mL TO ABOUT 100 mg/mL | 2 ~ 20 mg/mL |
| TRANSFERRIN | FROM ABOUT 1 ng/mL TO ABOUT 100 mg/mL | 0.1 ~ 1 mg/mL |

CULTURE MEDIA FOR MULTIPOTENT STEM CELLS

CROSS REFERENCE TO RELATED APPLICATIONS

The current application is a continuation and claims priority to International Patent Application Serial No.: PCT/2017/030410 filed on May 1, 2017, titled "CULTURE MEDIA FOR MULTIPOTENT STEM CELLS," which is a continuation in part and claims priority to co-pending application Ser. No. 15/142,135 filed on Apr. 29, 2016, entitled "CULTURE MEDIA FOR MULTIPOTENT STEM CELLS," which is also a continuation in part and claims priority to co-pending application Ser. No. 15/460,111 filed on Mar. 15, 2017, entitled "METHOD FOR GENERATING PROTEIN RICH CONDITIONED MEDIUM". These references are hereby incorporated in their entirety.

FIELD

The present embodiments generally relate to culture media used for culturing mesenchymal stem cells (MSCs).

BACKGROUND

Stem cells are cells that have the potential to develop into different cell types in the body during early life and growth. They have the ability to self-renew and are integral in the body's natural repair process. There are two primary sources of stem cells, embryonic and non-embryonic or adult stem cells. Adult stem cells are found in practically every tissue or organ in the body. They too have the ability to self-renew and differentiate into a multitude of specialized cell types.

Mesenchymal stem cells (MSCs) are a specific group of mesoderm origin adult stem cells that are pluripotent. Being pluripotent, they have multi-directional differentiation capabilities. They can become fat, bone, cartilage, tendons, muscle, nerves, ligaments, liver, cardiac muscle, endothelial cells, pancreatic islet cells and many other things. In addition, they are cells with low immunogenicity and are naturally immune-modulatory cells. Given their versatility, MSCs have quickly become an ideal cell type used in therapeutics for degenerative and autoimmune conditions, amongst other ailments.

MSCs have the unique ability to navigate or "home" to areas of injury and/or degeneration. When the body is in need of repair it sends out signals to mobilize stem cells to begin the repair process. MSCs not only differentiate but increase angiogenesis and excrete anti-inflammatory cytokines and growth factors. MSCs were originally found in bone marrow. It was soon discovered that in elderly or ill adults, the MSC content in bone marrow is extremely low. Low stem cell yield and a painful donation process led scientists to look for other, more easily available sources of MSCs in the body.

While the present disclosure deals with MSCs from any source, the current state of the art suggests that MSCs derived from adipose tissue (body fat) are the easiest and most practical to harvest and culture for various uses. However, the present disclosure is intended to encompass MSCs derived from any source, such as bone marrow, umbilical cord tissue, molar cells, amniotic fluid, or any other source known to persons having ordinary skill in the art.

Adipose tissue (fat) contains approximately 100,000 MSCs per gram of fat. It is a naturally rich source of MSCs, and the MSCs harvested therefrom are mostly unaffected by age or the donor's condition. Fat is becoming very popular as a stem cell source because of stem cell quality, properties, ease of extraction, and in most cases, ample availability.

Having a large amount of fat tissue may translate into a high stem cell count but acquiring a large amount is a fairly invasive procedure. Liposuction often requires general anesthesia and vacuum suction. When machine suction is used, cells are often broken and injured during the extraction process. Therefore, small, localized syringe extractions are ideal. In a typical case, a 5 gram extraction of fat would yield approximately 500,000 MSCs. To reach therapeutic quantities of MSCs (in the millions or billions), in vitro cell culture is a suitable solution.

Culturing fat derived MSCs is currently much easier as compared to other MSCs. Adipose derived MSCs generally proliferate well and behave consistently regardless of the donor's age or condition.

However, when utilizing currently existing culturing methods, the MSC proliferative potential and characteristics are continuously decreased during prolonged culture. For example, it has been shown that expansion in culture leads to premature senescence (the process of aging characterized by continuous morphological and functional changes). Cells can become much larger with irregular and flat shape and the cytoplasm became more granular.

These senescence-associated effects are continuously acquired from the onset of in vitro culture. As a result, the successful manufacturing for commercialization of large batches from one donor of homogenous MSCs that preserve their characteristics following expansion in culture remains a challenge.

Methods for increasing proliferation and survival in MSCs have been widely studied over the past few years and many factors have been proposed for increasing the expansion efficiency of these cells.

For example, many protocols relating to the expansion of MSCs include culturing in the presence of basic fibroblast growth factor (b-FGF). It has been shown that b-FGF not only maintains MSC proliferation potential, but it also retains osteogenic, adipogenic and chondrogenic differentiation potentials through the early mitogenic cycles. Vascular endothelial growth factor (VEGF) has also been shown to increase MSC proliferation. Hepatocyte growth factor (HGF) has been shown to affect proliferation, migration and differentiation. Platelet derived growth factor (PDGF) has been shown to be a potent mitogen of MSCs. Epidermal growth factor (EGF) and heparin-binding EGF have both been shown to promote ex vivo expansion of MSCs without triggering differentiation into any specific lineage. In addition to its mitogenic effect on MSCs, EGF also increases the number of colony-forming units by 25 percent.

The present disclosure makes use of a new growth medium which allows for MSC proliferation without the MSC characteristics being continuously decreased during prolonged culture. As such, a greater quantity of stable MSCs can be achieved in culture.

The present disclosure allows for rapid and efficient culture of mesenchymal stem cells without degradation of stem cell characteristics over time.

BRIEF DESCRIPTION OF THE DRAWINGS

The detailed description will be better understood in conjunction with the accompanying drawings as follows:

FIG. 1 is an example embodiment of the growth medium.

FIG. 2 is an example embodiment of the growth medium with optional component ingredients.

FIG. 3 is an example embodiment of an attachment medium.

The present embodiments are detailed below with reference to the listed Figures.

DETAILED DESCRIPTION OF THE EMBODIMENTS

Before explaining the present invention in detail, it is to be understood that the invention is not limited to the specifics of particular embodiments as described and that it can be practiced, constructed, or carried out in various ways.

While embodiments of the disclosure have been shown and described, modifications thereof can be made by one skilled in the art without departing from the spirit and teachings of the disclosure. The embodiments described herein are exemplary only, and are not intended to be limiting.

Specific structural and functional details disclosed herein are not to be interpreted as limiting, but merely as a basis of the claims and as a representative basis for teaching persons having ordinary skill in the art to variously employ the present invention. Many variations and modifications of embodiments disclosed herein are possible and are within the scope of the present disclosure.

Where numerical ranges or limitations are expressly stated, such express ranges or limitations should be understood to include iterative ranges or limitations of like magnitude falling within the expressly stated ranges or limitations.

The use of the word "a" or "an" when used in conjunction with the term "comprising" in the claims and/or the specification may mean "one," but it is also consistent with the meaning of "one or more," "at least one," and "one or more than one."

The word "about" means plus or minus 5 percent of the stated number.

The use of the term "optionally" with respect to any element of a claim is intended to mean that the subject element is required, or alternatively, is not required. Both alternatives are intended to be within the scope of the claim. Use of broader terms such as comprises, includes, having, etc. should be understood to provide support for narrower terms such as consisting of, consisting essentially of, comprised substantially of, and the like.

Accordingly, the scope of protection is not limited by the description herein, but is only limited by the claims which follow, encompassing all equivalents of the subject matter of the claims. Each and every claim is incorporated into the specification as an embodiment of the present disclosure. Thus, the claims are a further description and are an addition to the preferred embodiments of the present disclosure.

The inclusion or discussion of a reference is not an admission that it is prior art to the present disclosure, especially any reference that may have a publication date after the priority date of this application. The disclosures of all patents, patent applications, and publications cited herein are hereby incorporated by reference, to the extent they provide background knowledge; or exemplary, procedural or other details supplementary to those set forth herein.

The present embodiments generally relate to media used for culturing mesenchymal stem cells (MSCs). While human stem cells are the subject of the present disclosure, it is contemplated that all mammalian stem cells would respond to the culture as disclosed. In the spirit of enablement and clarity, human stem cells are utilized in this disclosure.

Serum, as used within this disclosure, refers to the remaining fraction after removal of coagulation and red blood cells from any mammalian blood. Exemplary serums used for cell culture as known to persons having ordinary skill in the art include, but are not limited to: fetal bovine serum (also known as fetal calf serum), horse serum, mouse serum, goat serum, rabbit serum, rat serum, human serum, and the like. Serum is also intended to encompass synthetic or recombinant equivalents, or other equivalents as known to persons having ordinary skill in the art, such as human platelet lysate (hPL).

Fibroblast growth factors and epidermal growth factors, as used within this disclosure, refers to families of proteins, hormones, or other naturally occurring substances that promote cell growth, proliferation, and/or differentiation. Members are typically involved in angiogenesis, wound healing, embryonic development, and various endocrine signaling pathways. Synthetic, recombinant, or other equivalents are also covered within the scope of this disclosure.

Pituitary extract, as used within this disclosure, refers to hormones extracted from the pituitary gland, such as oxytocin or vasopressin. Any mammalian pituitary extracts and their equivalents can be utilized. Synthetic, recombinant, or other equivalents are also covered within the scope of this disclosure.

L-cysteine, as used within this disclosure, refers to the amino acid as known to persons having ordinary skill in the art. Synthetic, recombinant, or other equivalents are also covered within the scope of this disclosure.

Glutathione, as used within this disclosure, refers to an antioxidant found in plants, animals, fungi, bacteria, or other living organisms. Synthetic, recombinant, or other equivalents are also covered within the scope of this disclosure.

N-acetyl cysteine (NAC), as used within this disclosure, refers to a protein that potentially participates in self-renewal and pluripotency in stem cells. Synthetic, recombinant, or other equivalents are also covered within the scope of this disclosure.

Selenium, as used within this disclosure, refers to the non-metal chemical element with the symbol Se. Synthetic, recombinant, or other equivalents are also covered within the scope of this disclosure.

Stromal-derived factor, as used within this disclosure, refers to proteins belonging to the chemokine family which promote growth, survival, and development of stem cells. Synthetic, recombinant, or other equivalents are also covered within the scope of this disclosure.

Sodium pyruvate, as used within this disclosure, refers to a compound commonly added to cell culture media to provide an additional source of energy. Synthetic, recombinant, or other equivalents are also covered within the scope of this disclosure.

Transferrin, as used within this disclosure, refers to iron binding proteins commonly found in blood. Any mammalian transferrin and equivalents can be utilized. Synthetic, recombinant, or other equivalents are also covered within the scope of this disclosure.

Serum-free medium, as used within this disclosure, refers to a basal medium. A basal medium can be any medium designed to support the growth of microorganisms or cells.

The present disclosure relates to a growth medium for culturing mesenchymal stem cells in a container. Any container known to persons having ordinary skill in the art can be utilized. The growth medium can comprise a serum, a fibroblast growth factor, and either an L-cysteine, a glutathione, or a N-acetyl cysteine (NAC). While this disclosure emphasizes the use of adipose derived stem cells, any MSC can be utilized for culture.

Optionally, the growth medium can also contain various quantities of an epidermal growth factor, a hydrocortisone, a calcium chloride, an insulin, a pituitary extract, a selenium, a stromal-derived factor, a sodium pyruvate, a transferrin, and serum-free medium.

Example Embodiment

Human adipose tissue-derived mesenchymal stem cells are cultured with a first growth medium containing fetal bovine serum, a fibroblast growth factor, and either L-cysteine, glutathione, or NAC in a normal cell culture environment. Temperature is maintained at 37 degrees Celsius, with a carbon dioxide concentration of 5 percent.

The above embodiment describes a typical environment for the culture of mesenchymal stem cells. Below are example embodiments suitable for culturing human MSCs:

To make another embodiment of the disclosed medium, combine ingredients in the following proportions: approximately 10 percent by volume of a serum, about 1 ng/mL to about 10 ng/mL of a fibroblast growth factor, about 1 ng/mL to about 10 ng/mL of an epidermal growth factor, about 10 ng/mL to about 100 ng/mL of hydrocortisone, about 0.01 mM to about 0.1 mM concentration of Calcium Chloride, about 0.5 mg/mL to about 5 mg/mL of insulin, about 10 μg/mL to about 100 μg/mL of pituitary extract, about 0.5 mM to about 5 mM concentration of L-Cysteine, about 0.1 μg/mL to about 1 μg/mL of selenium, about 1 ng/mL to about 10 ng/mL of a stromal derived factor, about 2 mg/mL to about 20 mg/mL of sodium pyruvate, about 0.1 mg/mL to about 1 mg/mL of transferrin. A basal medium can be used to balance the solution to 100 percent volume.

If powder form ingredients are used, they should to be dissolved in a salt buffered solution such as distilled deionized water (DDW), phosphate buffered saline (PBS), Dulbecco's phosphate buffered solution (DPBS), Hanks' Balanced Salt Solution (HBSS), Earle's Balanced Salt Solution (EBSS), and the like. To use the ingredients, the stock solutions can be prepared at 100-1000 times the needed concentration. Each stock solution should then be filtered. The filtered stock solutions should be stored at either room temperature or refrigerated temperature (2-8° C.) or freezing (−20° C.).

Equivalent ingredients, as discussed above, can be substituted.

Mesenchymal stem cells can be harvested and isolated using any techniques known to persons having ordinary skill in the art. MSCs can be seeded in a culture flask using an attachment medium. An attachment medium can be created by substituting a minimum essential medium (MEM), such as α-MEM, or a low glucose Dulbecco's modified eagle medium (DMEM) for the basal medium. For the purposes of this disclosure, minimum essential medium shall refer all such basal media known to persons having ordinary skill in the art.

DMEM is a modification of Basal Medium Eagle (BME) that contains a four-fold higher concentration of amino acids and vitamins, as well as additional supplementary components. Basal Medium Eagle (BME) is a widely used synthetic basal medium for supporting the growth of many different mammalian cells. BME was originally developed by Harry Eagle for HeLa cells and mouse fibroblasts, when he discovered the minimum requirements for cell growth in vitro. BME has since been used for other human lines.

MSCs can be expanded utilizing the following procedure:

After an incubation period, it should be confirmed that the cells have attached using an inverted microscope. All non-adherent cells, such as red blood cells, white blood cells, macrophages and pre-adipocytes, etc., should be discarded. The culture flask can be washed with PBS or DPBS, and the disclosed growth media (For T75-flask 10~15 mL and for T25-flask 3~7 mL) can be added to the flask to achieve the first expansion passage or P0.

The flask can be placed into an incubator at 5% CO2 and 37° C. The disclosed growth media can be changed every 2 days, or other desired time period. When a desired confluence is achieved, the old media is discarded. The flask can be washed with PBS or DPBS (for T75-flask 5~7 mL and for T25-flask 3~5 mL). TRYPLE™ Select solution (Life Technologies) can be added to the flask (For T75-flask 3 mL and for T25-flask 1 mL) and incubated at 5% CO2 and 37° C. for 3 minutes.

Once cells are confirmed to be detached from the bottom of the flask, PBS or DPBS can be added at the same amount as the TRYPLE™ Select solution to neutralize the enzyme. A small sample can be taken to count the cell number. The remaining cells can be centrifuged, and the supernatant discarded, leaving a cell pellet. According to the desired cell number or use, the cells can be divided for subculture to P1 or cryopreservation.

For subculture to P1, the cells can be resuspended in the disclosed growth media. When seeding a T175 flask, at least 1.5×106 cells are required and a Triple-flask will need at least 4.5×106 cells. The amount of disclosed growth media used will also depend on flask size. For a T175-flask, approximately 24~30 mL is used and for a Triple-flask, approximately 90~100 mL is used. This subculture process may be repeated to achieve the desired cell amounts.

For cryopreservation, the cells can be resuspended with a freezing solution comprised of disclosed growth media and 10% dimethyl sulfoxide (DMSO). 1.0×106~1.0×107 cells/mL can be transferred into each cryovial. Using a controlled rate freezer (CRF), the cells can be slowly cryopreserved. When complete, the cells can be transferred to vapor type liquid nitrogen storage tank for indefinite storage.

Cryopreserved cells can be thawed and sub-cultured using the same method above. When thawing, the cryovials can be placed in a water bath. After thawing, the cells can be transferred to a conical tube containing the disclosed growth media and centrifuged. After centrifugation, the top layer can be discarded and the cells re-suspend with disclosed growth media. The cells can be seeded onto the appropriate culture flasks.

Example 1—Methods

Proliferation comparison. After harvesting MSCs, MSCs are seeded into culture vessels at 1×106 cells/T75 flask with MesenCult-XF media (STEMCELL Technologies Inc.), MSC Growth media (ATCC), MesenPRO-RS (Invitrogen), MSC Growth media (Cell Applications Inc.), Bulletkit-ADSC media (Lonza), StemLine MSC Expansion media (Sigma-Aldrich), or the growth media disclosed here, to a total of eight T75-flasks. The cells can be incubated at 37° C. in 5% CO2. All media will be changed approximately every two days.

For morphology and cell proliferation comparison, pictures are taken at day 2 and day 5, and the number of cells is counted by trypan blue dye exclusion method at day 5.

Adipogenic differentiation induction of expanded MSCs. After harvesting MSCs, MSCs are seeded into culture vessels at 1×104 cells/cm2. For classical stain differentiation assay, cells are seeded into a multi-well plate. The cells are incubated in this growth media at 37° C. in 5% CO2 for a minimum of two hours up to four days.

Media is replaced with Complete Adipogenesis Differentiation Medium and continue incubation. MSCs will continue to undergo limited expansion as they differentiate under adipogenic conditions. Cultures are re-fed every ~3-4 days.

After specific periods of cultivation, adipogenic cultures can be processed for Oil Red O staining (beginning at ~7-14 days).

Chondrogenic differentiation induction of expanded MSCs. After harvesting MSCs, the cell pellet is resuspended in an appropriate volume of new growth media to generate a cell solution of 1.6×107 viable cells/mL.

Micromass cultures are generated by seeding 5 µL droplets of cell solution in the center of multi-well plate wells for classical staining.

After cultivating micromass cultures for 2 hours high humidity conditions, Complete Chondrogenesis Medium is added to culture vessels and incubated in 37° C. incubator with 5% CO2. Cultures are re-fed every ~2-3 days.

After specific periods of cultivation, chondrogenic pellets can be processed for Toluidine Blue O staining (>14 days).

Osteogeneic differentiation induction of expanded MSCs. After harvesting MSCs, MSCs are seeded into culture vessels at 5×103 cells/cm2. For classical stain differentiation assay, cells are seeded into a multi-well plate. The cells are seeded in new growth media at 37° C. in 5% CO2 for a minimum of two hours up to four days.

Media is replaced with Complete Osteogenesis Differentiation Medium and incubation continued. MSCs will continue to expand as they differentiate under osteogenic conditions. Cultures are re-fed every ~3-4 days.

After specific periods of cultivation, osteogenic cultures can be processed for Alizarin Red S staining (>21 days).

Immunological characteristic analysis of expanded MSCs. One of the problems with ex vivo expansion of stem cells is decrease in quality and cell characteristics over many passages. Thus, the expanded Ad-MSC will also undergo a surface antigen analysis to determine retained stem cell characteristics. Ad-MSC express CD73, CD90, and CD105 but lack expression of the hematopoietic lineage markers, CD34, CD45, and human leukocyte antigen-DR. The surface antigens will be tested using flow cytometry.

The cells will be washed with PBS and treated with TRYPLE™ Select before being centrifuged at 1700 rpm for 5 minutes. The supernatant will be discarded and the MSC pellet will be wash with 2% FBS or human serum and PBS before being centrifuged again. The supernatant will again be removed and discarded. The cells will be suspended in PBS and mixed with an antibody, FITC (fluorescein isothiocyanate), PE (phycoerythrin), APC (allo-phycocyanin), APC/Cy7, PerCP-Cy5.5. Brilliant Violet 421, etc. The cells/antibody mixture will be incubated on ice for at least 40 min before being centrifuged for 5 minutes, followed by the PBS wash step. The final cell pellet can be fixed with 1% paraformaldehyde and introduced into the flow cytometer.

In the flow cytometer, the cells will pass single-file through a laser beam as the cytometer records how the cells scatter the incident light and emit fluorescence. This will allow for analysis of the surface molecule at the single-cell level.

Example 2—Results

Morphology and Proliferation comparison. Ad-MSCs of all culture conditions displayed a characteristic fibroblast-like morphology at day 2. However, cells cultured by the disclosed growth media appeared smaller and more homogeneous spindle fibroblast-like morphology in comparison to other well-known manufacturer's media at day 5. Also at day 5, the confluency of Ad-MSCs cultured by the disclosed growth media observed much higher than other well-known manufacturer's media. As shown in, between days 0 and 5, the proliferation rate of Ad-MSCs cultured by the disclosed media was 2 to 10 times higher than other well-known manufacturer's media.

Multilineage differentiation induction of expanded MSCs. The multilineage differentiation capability of Ad-MSCs was examined by culturing cells collected under condition favorable for adipogenic, chondrogenic, and osteogenic differentiation. Adipogenesis and lipid vacuole formation in the MSCs were studied by staining cells with Oil Red O. At day 14 post adipogenic inductions, MSCs contained large Oil Red O positive lipid droplets within their cytoplasm. Chondrogenesis in MSCs was confirmed by staining chondrogenic proteoglycan (GAG, glycosaminoglycan) with Toluidine Blue O. At day 14 post chondrogenic inductions, chondrogenesis was characterized by the presence of strongly stained Toluidine Blue O positive. Osteogenesis in MSCs was stained with Alizarin Red S to determine calcium deposition. The cellular morphology changed from spindle shape to cuboid shape. At day 21 post osteogenic inductions, high level of osteogenesis was characterized by the presence of strongly stained Alizarin Red S positive nodular structures with well-defined inter-nodular regions not containing cells.

Immunological characteristic analysis of expanded MSCs. The expression of cell surface markers was analyzed by flow cytometry. All Ad-MSCs were highly positive for mesenchymal stromal cells surface markers including CD73 (99.25%), CD90 (98.88%), and CD105, and were negative for the hematopoietic and endothelial markers including CD34(1.29%), CD45(6.39%), and HLA-DR(1.57%).

Turning now to the Figures, FIG. 1 is an example embodiment of the growth medium. Listed are general component ranges for various components usable as the first growth medium, as well as a sample embodiment. It should be understood that the range limits can vary by five percent of the stated value.

FIG. 2 is an example embodiment of the growth medium with optional component ingredients. It should be understood that the range limits can vary by five percent of the stated value.

FIG. 3 is an example embodiment of an attachment medium. It should be understood that the range limits can vary by five percent of the stated value.

While the invention has been described with emphasis on the presented embodiments and Figures, it should be understood that within the scope of the appended claims, the invention might be practiced other than as specifically enabled herein.

What is claimed is:

1. A growth medium for culturing mesenchymal stem cells comprising:
   a) a serum from about 1 percent to about 10 percent by volume;
   b) a fibroblast growth factor from about 1 g/mL to about 10 ng/mL; and
   c) either:
      i) an L-cysteine from about 0.5 mM to about 5 mM; or
      ii) a glutathione from about 0.5 mM to about 5 mM;
   d) an epidermal growth factor from about 1 ng/ml to about 10 ng/ml;

e) hydrocortisone from about 10 ng/mL to about 100 ng/mL;
f) calcium chloride from about 0.01 mM to about 0.1 mM;
g) insulin from about 0.5 mg/mL to about 5 mg/mL;
h) pituitary extract from about 10 µg/mL to about 100 µg/mL;
i) selenium from about 0.1 µg/mL to about 1 µg/mL;
j) stromal-derived factor from about 1 ng/mL to about 10 ng/mL;
k) sodium pyruvate from about 2 mg/mL to about 20 mg/mL;
l) transferrin from about 0.1 mg/mL to about 1 mg/mL; and
m) serum free medium balanced to 100 percent volume; and wherein, a cultured mesenchymal stem cell is morphologically identical to a mesenchymal stem cell of a previous generation.

2. The stem cell growth medium of claim 1, wherein the serum is human serum.

3. The stem cell growth medium of claim 1, wherein the serum is fetal bovine serum.

4. The stem cell growth medium of claim 1, wherein at least one of the fibroblast growth factor or the epidermal growth factor is recombinant.

5. The stem cell growth medium of claim 1, wherein the stromal-derived factor is recombinant stromal-derived factor.

6. The stem cell growth medium of claim 1, wherein at least one of the insulin or the transferrin is recombinant.

7. The stem cell growth medium of claim 1, wherein said medium contains L-cysteine.

8. The stem cell growth medium of claim 1, wherein said medium contains glutathione.

* * * * *